United States Patent
Fang et al.

(10) Patent No.: US 11,248,032 B2
(45) Date of Patent: Feb. 15, 2022

(54) METHOD FOR PRODUCING SOLUBLE RECOMBINANT HUMAN-BASIC FIBROBLAST GROWTH FACTOR (RH-BFGF)

(71) Applicant: ZHUHAI ESSEX BIO-PHARMACEUTICAL CO., LTD., Guangdong (CN)

(72) Inventors: Haizhou Fang, Guangdong (CN); Bo Yang, Guangdong (CN); La Ma, Guangdong (CN); Peimin Dai, Guangdong (CN); Xinzhi Wang, Guangdong (CN); Malcolm Ngiam, Hong Kong (CN); Qi Xue, Hong Kong (CN); Yongjun Yang, Guangdong (CN)

(73) Assignee: ZHUHAI ESSEX BIO-PHARMACEUTICAL CO., LTD., Guangdong (CN)

( * ) Notice: Subject to any disclaimer, the term of this patent is extended or adjusted under 35 U.S.C. 154(b) by 0 days.

(21) Appl. No.: 16/625,191

(22) PCT Filed: Jun. 23, 2017

(86) PCT No.: PCT/CN2017/089810
§ 371 (c)(1),
(2) Date: Dec. 20, 2019

(87) PCT Pub. No.: WO2018/232745
PCT Pub. Date: Dec. 27, 2018

(65) Prior Publication Data
US 2020/0140509 A1  May 7, 2020

(51) Int. Cl.
*C07K 14/50* (2006.01)
*C12N 15/70* (2006.01)
*A61P 27/02* (2006.01)
*C12P 21/00* (2006.01)
*A61K 38/00* (2006.01)

(52) U.S. Cl.
CPC ............ *C07K 14/503* (2013.01); *A61P 27/02* (2018.01); *C12N 15/70* (2013.01); *C12P 21/00* (2013.01); *A61K 38/00* (2013.01)

(58) Field of Classification Search
None
See application file for complete search history.

(56) References Cited

U.S. PATENT DOCUMENTS

| 7,186,526 B2 * | 3/2007 | Fiddes | A61K 38/1825 |
| | | | 435/243 |
| 7,811,786 B1 * | 10/2010 | Lee | C12N 15/70 |
| | | | 435/69.1 |
| 2010/0062490 A1 * | 3/2010 | Werther | C07K 17/06 |
| | | | 435/69.7 |

FOREIGN PATENT DOCUMENTS

| CN | 1448510 A | 10/2003 |
| CN | 102585010 A | 7/2012 |
| CN | 102688479 A | 9/2012 |
| TW | 201621046 A | 6/2016 |
| WO | 2016108240 A1 | 7/2016 |

OTHER PUBLICATIONS

International Search Report for corresponding International Application No. PCT/CN2017/095643 dated Apr. 26, 2018.
European Patent Office Extended Search Report for Application No. 17915171.7 dated Feb. 15, 2021 (11 pages).
European Patent Office Partial Supplementary Search Report for Application No. 17915171.7 dated Mar. 15, 2021 (12 pages).
Soleyman et al., "High-level Expression and Purification of Active Human FGF-2 in *Escherichia coli* by Codon and Culture Condition Optimization", Iran Red Crescent Med J., vol. 18, No. 2, 2016, pp. e21615, 18 pages.
Japanese Patent Office Notice of Reasons for Refusal for Application No. 2020520690 dated May 25, 2021 (14 pages including English translation).

* cited by examiner

*Primary Examiner* — Marianne P Allen
(74) *Attorney, Agent, or Firm* — Michael Best & Friedrich LLP

(57) ABSTRACT

Provided are a method for producing a soluble recombinant human-basic fibroblast growth factor (rh-bFGF), a recombinant human-basic fibroblast growth factor (rh-bFGF) obtained by the method, and a mutated nucleic acid molecule encoding the recombinant human-basic fibroblast growth factor (rh-bFGF).

7 Claims, 5 Drawing Sheets
Specification includes a Sequence Listing.

bFGF-0911
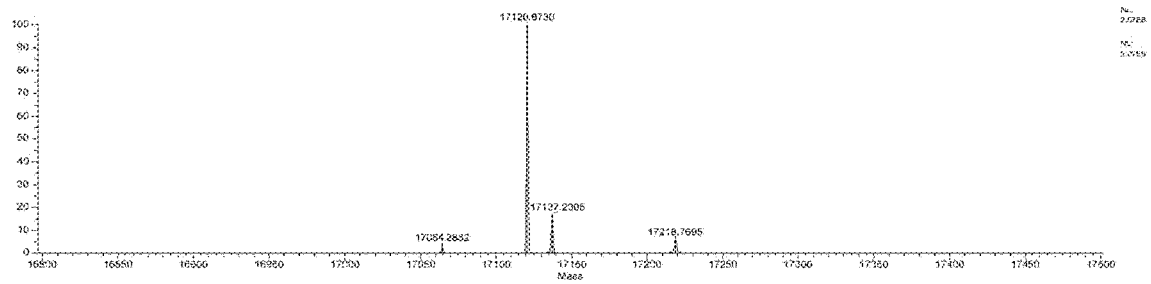
bFGF-0912
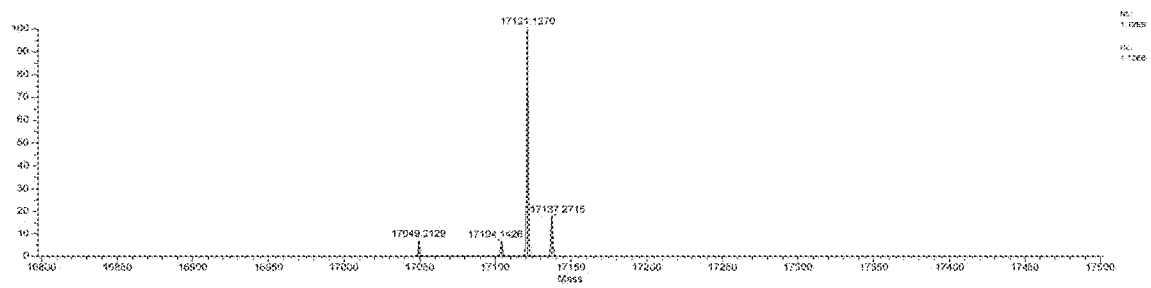
bFGF-0913
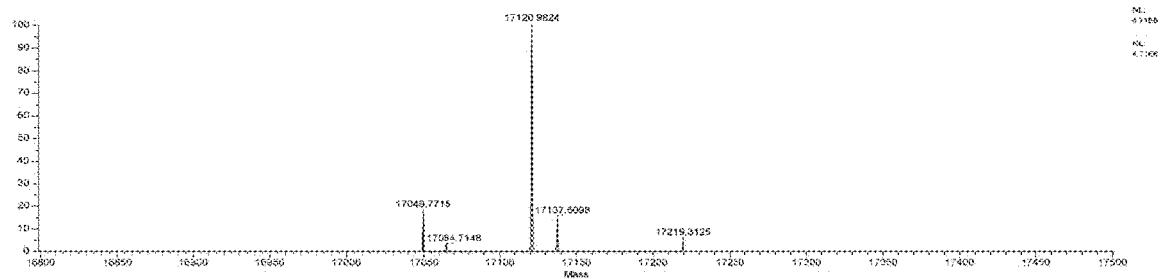
bFGF-1001
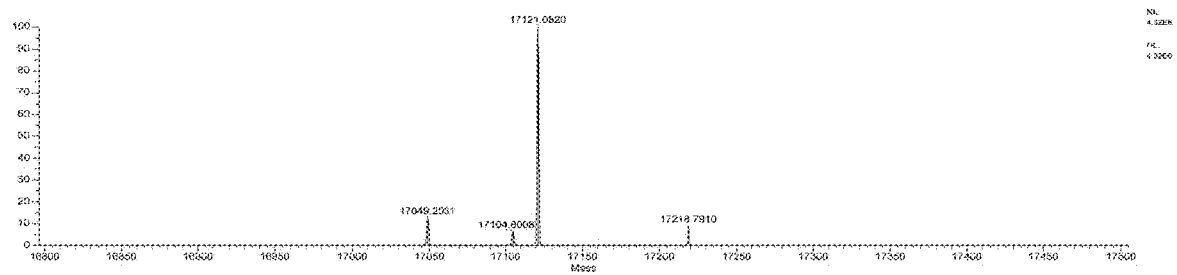
Figure 4 atg gca gcc ggg agc atc acc acg ctg ccc gcc ttg ccc gag gat ggc ggc agc ggc gcc ttc ccg ccc ggc cac ttc aag gac ccc aag cgg ctg tac tgc aaa aac ggg ggc ttc ttc ctg cgc atc cac ccc gac ggc cga gtt gac ggg gtc cgg gag aag agc gac cct cac atc aag cta caa ctt caa gca gaa gag aga gga gtt gtg tct atc aaa gga gtg tgt gct aac cgt tac ctg gct atg aag gaa gat gga aga tta ctg gct tct aaa tgt gtt acg gat gag tgt ttc ttt ttt gaa cga ttg gaa tct aat aac tac aat act tac cgg tca agg aaa tac acc agt tgg tat gtg gca ctg aaa cga act ggg cag tat aaa ctt gga tcc aaa aca gga cct ggg cag aaa gct ata ctt ttt ctt cca atg tct gct aag agc tga

Native human bFGF cDNA sequence (SEQ ID NO:4)

| 1 | maagsittlp | alpedggsga | fppghfkdpk | rlycknggff | lrihpdgrvd | gvreksdphi |
| 61 | klqlqaeerg | vvsikgvcan | rylamkedgr | llaskcvtde | cffferlesn | nyntyrsrky |
| 121 | tswyvalkrt | gqyklgsktg | pgqkailflp | msaks | | |

Amino acid sequence of native human bFGF (SEQ ID NO:5)

| 1 | maagsittlp | alpedggsga | fppghfkdpk | rlycknggff | lrihpdgrvd | gvreksdphi |
| 61 | klqlqaeerg | vvsikgvcan | rylamkedgr | llaskcvtde | cffferlesn | nyntyrsrky |
| 121 | tswyvalkrt | gqyklgsktg | pgqkailflp | msaks | | |

Human bFGF amino acid sequence (SEQ ID NO:6) produced by the present mutated nucleic acid molecules

Figure 5

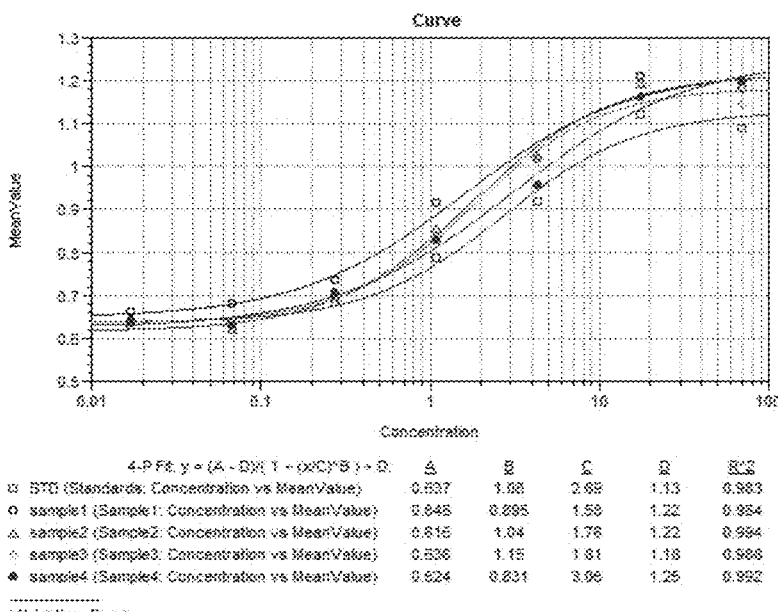

Figure 6

METHOD FOR PRODUCING SOLUBLE RECOMBINANT HUMAN-BASIC FIBROBLAST GROWTH FACTOR (RH-BFGF)

CROSS REFERENCE TO RELATED APPLICATIONS

This patent application is the U.S. national stage entry, under 35 U.S.C. § 371, of International Application No. PCT/CN2017/089810, filed Jun. 23, 2017, the entire contents of which are hereby incorporated by reference.

SEQUENCE LISTING

The sequence listing is filed with the application in electronic format only and is incorporated by reference herein. The sequence listing text file "023704-9013-US01_As_Filed_Sequence_Listing.txt" was created on Dec. 19, 2019 and is 6,008 bytes in size.

TECHNICAL FIELD

The invention relates to the field of DNA recombination and biopharmaceuticals. More specifically, the invention relates to a method for producing a soluble recombinant human-basic fibroblast growth factor (rh-bFGF), a recombinant human-basic fibroblast growth factor (rh-bFGF) obtained by the method, and a mutated nucleic acid molecule encoding the recombinant human-basic fibroblast growth factor (rh-bFGF).

BACKGROUND TECHNIQUE

Fibroblast growth factors (FGFs) are a class of heparin-binding proteins with similar structures and similar biological functions. At present, 23 kinds of FGFs have been found, of which FGF-1 (aFGF), FGF-2 (bFGF) and FGF-7 (KGF) have been studied more in-depth. bFGF is an active substance in a very small amount in mammals and humans, and is highly valued for its wide physiological functions and important clinical application value. It not only stimulates the formation of new blood vessels, but also participates in wound healing and tissue regeneration, and promotes the development and differentiation of embryonic tissues. In recent years, recombinant bFGFs have been used in the clinical treatment of diseases such as trauma, ulcers and nervous system diseases.

At present, most of the bFGFs on the market are produced in *Escherichia coli* (*E. coli*) by genetic engineering, but the expression of soluble bFGFs by *E. coli* is low in level, and most of the expressed products are easy to form non-biologically active inclusion bodies. After the inclusion bodies are purified, they need to be renatured, which affects the recovery and activity of the products. Moreover, the treatment process may result in the formation of impurities such as dimers and trimers. In addition, bFGF has two pairs of cysteines, which easily form intermolecular disulfide bonds. If stored improperly, dimers and trimers will account for a certain proportion, which will affect the purity of the protein.

Therefore, there is a need to establish a stable new method for producing soluble bFGFs with a high expression level.

SUMMARY OF THE INVENTION

In one aspect, the invention provides a method of producing a soluble recombinant human-basic fibroblast growth factor (rh-bFGF) comprising: culturing a host cell comprising a mutated nucleic acid molecule; expressing the rh-bFGF in the host cell under a condition suitable for expression of the rh-bFGF; and recovering the rh-bFGF by purification.

In one aspect, the invention provides a recombinant human-basic fibroblast growth factor (rh-bFGF) obtained by the method.

In one aspect, the invention provides a mutated nucleic acid molecule encoding the recombinant human-basic fibroblast growth factor (rh-bFGF).

In one aspect, the invention provides a pharmaceutical composition comprising the recombinant human-basic fibroblast growth factor (rh-bFGF) and at least one pharmaceutically acceptable excipient.

In one aspect, the invention provides a method of treating dry eye, the method comprising administering to a patient in need thereof a therapeutically effective amount of the pharmaceutical composition.

DRAWINGS

FIG. 4 shows the molecular mass spectrum of the rh-bFGF intact protein.

FIG. 5 shows the cDNA sequence and amino acid sequence of the native human bFGF (SEQ ID NO: 5) and the amino acid sequence of the human bFGF (SEQ ID NO: 6) produced by the present mutated nucleic acid molecules.

FIG. 6 shows a four-parameter fitting curve for the assay of the rh-bFGF in vitro activity, where C is the EC50 value.

DETAILED DESCRIPTION OF THE INVENTION

Figure 1:
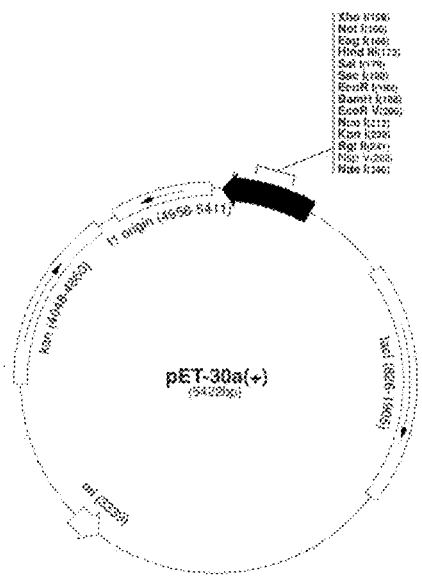
FIG. 1 is a diagram showing the structure of the pET-30a (+) plasmid.

The inventors of the present application have developed a novel method for producing a soluble recombinant human-basic fibroblast growth factor (rh-bFGF) by mutating a nucleic acid molecule.

The invention unexpectedly achieves a highly efficient and uniform expression of the bFGF in a soluble form and high expression level by mutating a nucleic acid molecule and constructing a prokaryotic expression system. This method enhances the recovery of the recombinant human bFGF protein by expressing the human bFGF in high efficacy, and retains the biological activity of the native human bFGF.

In one aspect, the invention provides a method of producing a soluble recombinant human-basic fibroblast growth factor (rh-bFGF) comprising: culturing a host cell comprising a mutated nucleic acid molecule; expressing the rh-bFGF in the host cell under a condition suitable for expression of the rh-bFGF; and recovering the rh-bFGF by purification.

In one aspect, the mutated nucleic acid molecule comprises a sequence selected from the group consisting of SEQ ID NO: 1, SEQ ID NO: 2 or SEQ ID NO: 3, or comprises a sequence having at least 90%, at least 95% identity, such as at least 96%, 97%, 98% or 99% identity to SEQ ID NO: 1, SEQ ID NO: 2 or SEQ ID NO: 3.

In one aspect, the sequence of the mutated nucleic acid molecule is SEQ ID NO: 1, SEQ ID NO: 2 or SEQ ID NO: 3.

In one aspect, the invention provides a vector comprising the nucleic acid molecule. A preferred vector is a prokaryotic expression vector, particularly an expression vector suitable for induction expression in *E. coli*, including but not limited to, for example, pET-30a(+), pET-28a(+), pET-23c(+), pET-15b. pET-30a(+) is particularly preferred.

In one aspect, the invention provides a host cell comprising the expression vector. A preferred host cell is *E. coli*, and *E. coli* BL21 (DE3) is particularly preferred.

In a specific aspect, the prokaryotic expression vector comprising the mutated nucleic acid molecule is transformed into *E. coli* BL21 (DE3), and the expression of the soluble human bFGF is induced by adjusting the bacterial culture temperature, the induction temperature, the pH range, the glucose concentration, and the inducer concentration. The bacteria are collected by washing and filtering through hollow fiber; the fermented bacteria are disrupted by using high-pressure homogenization and maintaining at a low temperature; after adding an appropriate amount of nonionic surfactant, the supernatant is collected by low-temperature high-speed centrifugation, and the pellet is discarded.

In a specific aspect, purification is carried out by use of a process such as weak cation exchange, heparin affinity chromatography or the like, and an appropriate amount of a protective agent such as mercaptoethanol, DTT or the like is added during the purification.

In a specific aspect, the specific parameters used to induce expression of the soluble human bFGF are as follows:
  OD600 before entering into the tank: about 0.5-4.5
  Bacterial culture temperature: about 25-45° C.
  Bacterial induction temperature: about 20-50° C.
  pH range: about 6.8-8.5
  Glucose concentration: about 0.06-0.46%
  Inducer concentration: about 0.0125-0.0925 g/L
  OD600 range before induction: about 10 to 45
  Induction time: about 2-9 h.

In a specific aspect, purification is carried out as follows:
  The fermentation broth is intercepted with hollow fiber and washed and filtered, and the washing buffer is a PB solution containing NaCl at a pH of about 7.0.

The fermented bacteria are disrupted by using high-pressure homogenization and maintaining at a low temperature; after adding an appropriate amount of Triton, the supernatant is collected by low-temperature high-speed centrifugation, and the pellet is discarded.

In one aspect, the invention provides a recombinant human-basic fibroblast growth factor (rh-bFGF) obtained by the method. In one aspect, the amino acid sequence of the recombinant human-basic fibroblast growth factor is SEQ ID NO:5.

In one aspect, the invention provides a mutated nucleic acid molecule encoding the recombinant human-basic fibroblast growth factor, comprising a sequence selected from the group consisting of SEQ ID NO: 1, SEQ ID NO: 2 or SEQ ID NO: 3, or comprising a sequence having at least 95%, 96%, 97%, 98% or 99% identity to SEQ ID NO: 1, SEQ ID NO: 2 or SEQ ID NO: 3.

In one aspect, the sequence of the mutated nucleic acid molecule is SEQ ID NO: 1, SEQ ID NO: 2 or SEQ ID NO: 3.

In one aspect, the invention provides a pharmaceutical composition comprising the recombinant human-basic fibroblast growth factor (rh-bFGF) and at least one pharmaceutically acceptable excipient. In one aspect, the excipient includes, but is not limited to, a buffer system, a thickener, a stabilizer, a neutralizing agent, a humectant, and the like.

In one aspect, the present invention provides a pharmaceutical composition comprising the recombinant human-basic fibroblast growth factor (rh-bFGF) and at least one stabilizer selected from the group consisting of glycine, histidine, arginine, heparin sodium or human serum albumin (HSA).

In one aspect, the composition is buffered to a pH of between about 6.0 and 8.0, such as a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0 or a pH defined by any range therebetween.

In one aspect, the invention provides a method of treating dry eye, the method comprising administering to a patient in need thereof a therapeutically effective amount of the pharmaceutical composition.

In one aspect, the invention provides the pharmaceutical composition for use in treating dry eye.

In one aspect, the invention also provides use of the composition in the manufacture of a medicament for treating dry eye.

In one aspect, the pharmaceutical composition of the invention is an ophthalmic pharmaceutical composition. In particular, the pharmaceutical composition of the invention is in the form of an eye drop or a gel.

An advantage of the method of the invention lies in that a high efficient and uniform expression of bFGF is achieved in a soluble form and high expression level. Such method enhances the recovery of the recombinant human bFGF protein by expressing the human bFGF in high efficacy, and retains the biological activity of the native human bFGF.

The invention is further described with reference to the following non-limiting examples.

EXAMPLE

Example 1. Nucleic Acid Mutation

The cDNA sequence (SEQ ID NO: 4) encoding the native human bFGF was mutated without changing the amino acid sequence of the protein, and three mutated cDNA sequences were designed and synthesized (mutated cDNA Sequence 1, Sequence 2 and Sequence 3 as showed by SEQ ID NO: 1, SEQ ID NO: 2 and SEQ ID NO: 3, respectively):

Mutated cDNA Sequence 1 (SEQ ID NO: 1)
atg gct gct ggt tcg att acg acg ctg ccg gct ctg ccg gaa gat ggt ggt tca ggt gca ttt ccg ccg ggt cac ttt aag gat ccg aaa cgt ctg tat tgc aag aac ggc ggc ttt ttc ctg cgc att cat ccg gat ggc cgt gtc gac ggt gtg cgc gaa aaa agc gat ccg cac att aag ctg cag ctg caa gca gaa gaa cgt ggc gtg gtt agc atc aaa ggt gtt tgt gcg aac cgt tac ctg gcc atg aaa gaa gat ggc cgc ctg ctg gct
agt aag tgc gtc acc gac gaa tgc ttt ttc ttt gaa cgt ctg gaa tcc
aac aat tat aat acc tac cgt agc cgc aaa tat acg tct tgg tat gtg
gcc ctg aaa cgc acg ggc cag tat aag ctg ggt tcc aaa acg ggt
ccg ggt caa aaa gcc att ctg ttc ctg ccg atg tcc gca aaa tca taa Mutated cDNA Sequence 2 (SEQ ID NO:2)
atg gct gct ggt tct atc acc acc ctg ccg gct ctg ccg gaa gac
ggt ggt tct ggt gctttc ccg ccg ggt cac ttc aaa gac ccg aaa cgt
ctg tac tgc aaa aac ggt ggt ttc ttc ctg cgt atc cac ccg gac ggt
cgt gtt gac ggt gtt cgt gaa aaa tct gac ccg cac atc aaa ctg cag
ctg cag gct gaa gaa cgt ggt gtt gtt tct atc aaa ggt gtt tgc gct
aac cgt tac ctg gct atg aaa gaa gac ggt cgt ctg ctg gct tct aaa
tgc gtt acc gac gaa tgc ttc ttc ttc gaa cgt ctg gaa tct aac aac
tac aac acc tac cgt tct cgt aaa tac acc tct tgg tac gtt gct ctg
aaa cgt acc ggt cag tac aaa ctg ggt tct aaa acc ggt ccg ggt cag
aaa gct atc ctg ttc ctg ccg atg tct gct aaa tct taa Mutated cDNA Sequence 3 (SEQ ID NO:3)
atg gca gcc ggt agc atc acc acc ctg ccg gcc ctg ccg gag gat
ggc ggc agc ggc gcc ttc ccg ccg ggc cac ttc aag gac ccg aag
cgt ctg tac tgc aaa aac ggt ggc ttc ttc ctg cgc atc cac ccg gac
ggc cgt gtt gac ggt gtc cgt gag aag agc gac cct cac atcaag ctg
caa ctg caa gca gaa gag cgt ggt gtt gtg tct atc aaa ggt gtg tgt
gct aac cgt tac ctg gct atg aag gaa gat ggt cgt ctg ctg gct tct
aaa tgt gtt acc gat gag tgt ttc ttt ttt gaa cgt ctg gaa tct aac aac
tac aac act tac cgt tct cgt aaa tac acc tct tgg tat gtg gca ctg
aaa cgt act ggt cag tat aaa ctg ggt tcc a aa acc ggt cct ggt cag
aaa gct atc ctg ttt ctg cca atg tct gct aag agc taa

Example 2. Prokaryotic Expression and Protein Characterization 2.1 Expression and Purification The expression vector used was pET-30a(+) (see FIG. 1) and was purchased from Merk KgsA co. (Cat. No. 69909-3). The vector carries a T7 promoter, a T7 transcription initiation site, a His Tag, a coding sequence, an S Tag coding sequence, multiple cloning sites (MCSs), a T7 terminator, a lactose coding sequence, a kan resistance coding sequence, and a pBR322 replicon and a f1 replicon. The MCSs comprise the restriction sites XhoI, NotI, EagI, HindIII, SalI, SacI, EcoRI, BamHI, EcoRV, NcoI, KpnI, BglII, NspV, and NdeI.

For ease of cloning, a NdeI restriction site was designed upstream of the start codon of the Sequence 1 (SEQ ID NO: 1) and a HindIII restriction site was designed near the terminator. The 480 bps sequence was achieved by gene synthesis through chemical method. The sequence was double-digested with NdeI and HindIII and then inserted into the same double-digested expression vector pET-30a(+) to obtain a 5724 bps recombinant plasmid, which was transformed into DH5α (TaKaRa, 9057) by heat shock method and cultured in LB medium containing 50 μg/mL kanamycin. Monoclones were selected and the correct transformants were screened by NdeI and HindIII double digestion. The correctness of the transformants was verified again by sequencing.

In another example, pET-28a(+), pET-23c(+) or pET-15b or the like can be used in place of the above pET-30a(+) vector.

The prokaryotic expression vector containing the Sequence 1 was transformed into E. coli BL21 (DE3), and the soluble human bFGF was induced to be expressed by culture, and the specific parameters were as follows:

OD600 before entering into the tank: 0.5-4.5
Bacterial culture temperature: 25-45° C.
Bacterial induction temperature: 20-50° C.
pH range: 6.8-8.5
Glucose concentration: 0.06-0.46%
Inducer concentration: 0.0125-0.0925 g/L
OD600 range before induction: 10 to 45
Induction time: 2-9 h.

The bacteria were collected by washing and filtering through hollow fiber: the fermentation broth was intercepted with 500 KD hollow fiber, and washed and filtered; the washing buffer was a 25 mM PB solution containing NaCl, pH 7.0.

The fermented bacteria were disrupted by using high-pressure homogenization and maintaining at a low temperature; after adding an appropriate amount of Triton, the supernatant was collected by low-temperature high-speed centrifugation, and the pellet was discarded.

A weak cation exchange was used, and an appropriate amount of DTT was added during the purification. The CM-Sepharose Fast Flow ion exchange column was first equilibrated with 25 mM phosphate buffer (pH 7.0) containing sodium chloride, and then the supernatant was passed through the column. Gradient (three gradients) elution was performed with 25 mM phosphate buffer (pH 7.0) containing 0.05 M, 0.12 M, and 0.4 M sodium chloride, and the third elution peak (eluting with 25 mM phosphate buffer containing 0.4 M sodium chloride) was collected.

Heparin affinity chromatography was used, and an appropriate amount of DTT was added during the purification. The Heparin-Sepharose CL-6B affinity chromatography column was pre-equilibrated with 25 mM phosphate buffer (pH 7.0) containing sodium chloride, and the solution of the third elution peak of the ion exchange chromatography was passed through the column. Gradient (three gradients) elution was performed with 25 mM phosphate buffer (pH 7.0) containing 0.4 M, 1.0 M, and 1.8 M sodium chloride, and the third elution peak (eluting with 25 mM phosphate buffer containing 1.8 M sodium chloride) was collected.

After the sample was purified by the above procedures, its purity was up to 95% and more. Experiments confirmed that about 600 mg of recombinant human bFGF protein could be prepared per 100 g of bacteria, and a significant high expression has been achieved.

2.2 Purity and Molecular Weight Detection and Sequencing

Figure 2:
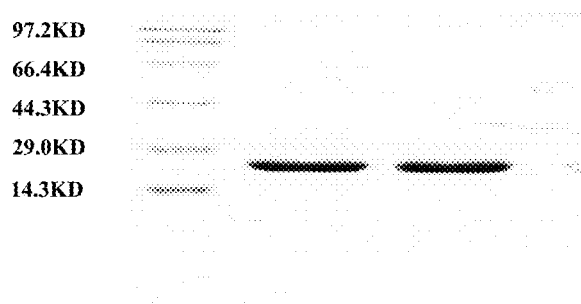
FIG. 2 shows the results of Western Blot of rh-bFGF.
Figure 3:
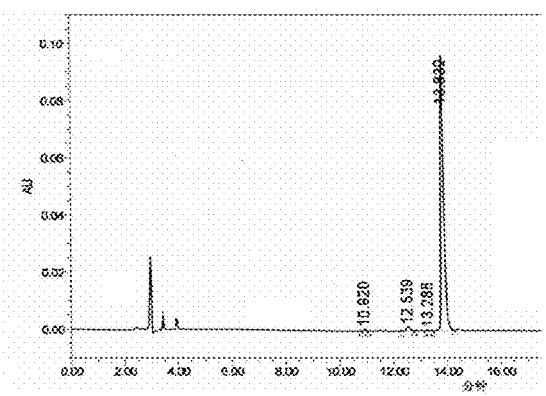
FIG. 3 shows the purity of rh-bFGF detected by high performance liquid chromatography.

15% SDS-PAGE electrophoresis showed that the human bFGF protein as obtained was a single band of approximately 18.5 KD (see FIG. 2). The detection results of the high performance liquid chromatography with a C8 reverse phase column showed that the purity of the human bFGF as obtained in the present invention was more than 95% (see FIG. 3).

"Ultra-high resolution, ultra-high accuracy, ultra-high sensitivity" Exactive Plus EMR was used for accurate molecular weight determination, and 6 components (components 1, 4, 5 ratios basically >10%, table 1) were detected in 4 batches of rh-bFGF stock solutions. Component 4 is the main component, and has an average molecular weight of 17121.02 Da; the inter-batch RSD % is 0.0007, with a deviation from the theoretical value of ≤41 ppm, and the relative ratio (calculated as peak intensity) is 70.7%-79.0%.

TABLE 1

HPLC-Exactive Plus EMR mass spectrometry for accurate molecular weight of test samples

| Component | Batch | Experimental value (Da) | Theoretical value (Da) | Deviation (ppm) | Relative ratio (%) | Mean | RSD % |
|---|---|---|---|---|---|---|---|
| 1 | Stock Batch II | 17049.21 | 17049.34Δ | 8 | 5.2 | 17049.40 | 0.0019 |
|  | Stock Batch III | 17049.77 |  | 25 | 12.6 |  |  |
|  | Physical-chemical standard | 17049.20 |  | 8 | 9.8 |  |  |
| 4 | Stock Batch I | 17120.87 | 17120.42* | 26 | 79.0 | 17121.02 | 0.0007 |
|  | Stock Batch II | 17121.13 |  | 41 | 76.6 |  |  |
|  | Stock Batch III | 17120.98 |  | 33 | 70.7 |  |  |
|  | Physical-chemical standard | 17121.08 |  | 39 | 78.5 |  |  |
| 5 | Stock Batch I | 17137.23 | 17136.42☐ | 47 | 13.4 | 17137.34 | 0.0009 |
|  | Stock Batch II | 17137.27 |  | 50 | 13.4 |  |  |
|  | Stock Batch III | 17137.51 |  | 64 | 10.6 |  |  |

In addition, the recombinantly prepared human bFGF protein (SEQ ID NO: 6) was analyzed for amino acid sequence, and it was confirmed that the amino acid sequence thereof was identical to that of native human bFGF (SEQ ID NO: 5; see FIG. 5).

2.3 Biological Activity Assay

The samples were tested for in vitro activity using balb/c3T3 cells. Cell proliferation was judged by MTT assay. The results showed that the effect of promoting proliferation of balb/c3T3 cells by the obtained human bFGF was consistent with that by the bFGF active standard (NISCB) (see FIG. 6).

Example 3. Preparation of Pharmaceutical Compositions

Pharmaceutical Composition 1:

| | |
|---|---|
| recombinant human-basic fibroblast growth factor | 2500-10000 IU; |
| human serum albumin | 0.025-0.375 mg/mL; |
| thickener | 5.0-15.0 mg/mL; |
| sodium chloride | 5.0-12.5 mg/mL; |
| heparin sodium | 0.25-5.0 μg/mL; |
| sodium dihydrogen phosphate | 0.25-1.25 mg/mL; |
| disodium hydrogen phosphate | 1.25-3.75 mg/mL. |

1. The buffer system may be the above sodium dihydrogen phosphate and disodium hydrogen phosphate, or a boric acid-borax buffer system, a citric acid-disodium hydrogen phosphate buffer system or the like. Preferably, the pharmaceutical composition has a pH of from 6.5 to 7.5.

2. The thickener is polyvinyl alcohol, sodium hyaluronate, hypromellose, poloxamer, or the like, and preferably polyvinyl alcohol.

3. Preparation procedure:

(1) Polyvinyl alcohol is dispersed and dissolved in an appropriate amount of water for injection, autoclaved at 121° C. for 30 min, cooled to room temperature, and ready for use;

(2) Recombinant human-basic fibroblast growth factor, human serum albumin, heparin sodium, sodium chloride, sodium dihydrogen phosphate, and disodium hydrogen phosphate are dissolved in an appropriate amount of water for injection, and sterile filtered through a 0.22 μm filter membrane;

(3) The solutions obtained in the step (1) and in the step (2) are uniformly mixed under a sterile condition, made up to the fixed volume with sterile water for injection, and thus obtained;

(4) The sterile solution is filled by using a three-in-one filling machine of blowing, filling and sealing, and the filling amount is 0.4 mL, and thus the finished product is obtained.

Pharmaceutical Composition 2:

| | |
|---|---|
| recombinant human-basic fibroblast growth factor | 2500-10000 IU; |
| human serum albumin | 0.1-0.375 mg/mL; |
| heparin sodium | 25.0-75.0 μg/mL; |
| carbomer | 1.25-12.5 mg/mL; |
| neutralizing agent | 1.25-12.5 mg/mL; |
| glycerol | 12.5-50 mg/mL. |

1. The carbomer is a series of Carbomer 940, Carbomer 934, Carbomer 974, Carbomer 980, etc., preferably a Carbomer 980 series;

2. The neutralizing agent is sodium hydroxide, potassium hydroxide, potassium hydrogen carbonate, borax and triethanolamine, preferably triethanolamine.

3. Preparation procedure:

(1) Carbomer is dispersed in an appropriate amount of water for injection, stirred uniformly, and then swelled overnight, and ready for use;

(2) Triethanolamine is added to the carbomer dispersion, stirred into a transparent uniform gel base, autoclaved at 121° C. for 30 min, cooled to room temperature after sterilization is completed, and ready for use;

(3) Glycerol, human serum albumin, heparin sodium, and recombinant human-basic fibroblast growth factor are added into an appropriate amount of room temperature water for injection, stirred uniformly, and then passed through a 0.22 μm filter membrane under a sterile condition, mixed with the gel base in the step (2), and then quantified and stirred uniformly;

(4) The sterile gel is filled by using a three-in-one filling machine of blowing, filling and sealing, and the filling amount is 0.4 g, and thus the finished product is obtained.

Pharmaceutical Composition 3:

| | |
|---|---|
| recombinant human-basic fibroblast growth factor | 1000-9000 IU |
| human serum albumin | 0.01-0.50 mg/mL; |
| thickener | 0.1-20.0 mg/mL; |
| sodium dihydrogen phosphate | 0.2-2.5 mg/mL; |
| disodium hydrogen phosphate | 0.5-5.0 mg/mL; |
| sodium chloride | 1.0-5.0 mg/mL; |
| humectant | 0.1-50.0 mg/mL. |

1. The buffer salt system may be the above sodium dihydrogen phosphate and disodium hydrogen phosphate, or a boric acid-borax buffer system, a citric acid-disodium hydrogen phosphate buffer system or the like; preferably, the pH is from 6.5 to 7.5.

2. The thickener is polyvinyl alcohol, sodium hyaluronate, hypromellose, poloxamer, or the like, and preferably polyvinyl alcohol. The humectant is glycerin, propylene glycol or a mixture thereof.

3. Preparation procedure:

(1) The thickener and sodium chloride are dispersed and dissolved in an appropriate amount of water for injection, and autoclaved at 121° C. for 30 min;

(2) Recombinant human-basic fibroblast growth factor, human serum albumin, humectant, sodium dihydrogen phosphate, and disodium hydrogen phosphate are dissolved in an appropriate amount of water for injection;

(3) The agent solution in the step (2) is filtered through a 0.22 μm microporous filter membrane and then mixed with the agent solution obtained in the step (1), and made up to 1 mL with water for injection;

(4) The agent solution obtained in the step (3) is filled into a packaging container containing no bacteriostatic agent, and the volume of the container is in the range of 0.4 g/piece, and thus, the finished product is obtained.

In addition, the following pharmaceutical compositions (see Table 2) were also prepared. Among them, the eye drops were prepared as 100 ml, and the external gels were prepared as 100 g.

(3) The solutions obtained in the step (1) and in the step (2) were uniformly mixed under a sterile condition, made up to 100 mL with sterile water for injection, and thus obtained.

(4) The sterile solution was filled by using a three-in-one filling machine of blowing, filling and sealing, and the filling amount was 0.4 mL, and thus the finished product was obtained.

Preparation Example 2

(1) 0.5 g of polyvinyl alcohol was dispersed and dissolved in an appropriate amount of water for injection, autoclaved, cooled to room temperature, and ready for use;

(2) 500000 IU of recombinant human-basic fibroblast growth factor, 20 mg of human serum albumin, 2.0 mg of heparin sodium, 800 mg of sodium chloride, 42.5 mg of sodium dihydrogen phosphate, and 250 mg of disodium hydrogen phosphate were dissolved in an appropriate amount of water for injection, and sterile filtered through a 0.22 μm filter membrane;

(3) The solutions obtained in the step (1) and in the step (2) were uniformly mixed under a sterile condition, made up to 100 mL with sterile water for injection, and thus obtained;

TABLE 2

Pharmaceutical compositions of Preparation Examples 1-10

|  | Preparation Example 1 | Preparation Example 2 | Preparation Example 3 | Preparation Example 4 | Preparation Example 5 |
|---|---|---|---|---|---|
| polyvinyl alcohol | 10.0 mg/mL | 10.0 mg/mL | 10.0 mg/mL | 10.0 mg/mL | 10.0 mg/mL |
| Carbomer 940 |  |  |  |  |  |
| triethanolamine |  |  |  |  |  |
| rh-bFGF | 5000 IU/mL | 5000 IU/mL | 4200 IU/mL | 4200 IU/mL | 4200 IU/mL |
| glycerol |  |  |  |  |  |
| human serum albumin | 0.25 mg/mL | 0.20 mg/mL | 0.20 mg/mL | 0.10 mg/mL | 0.20 mg/mL |
| heparin sodium | 25 μg/mL | 20 μg/mL | 20 μg/mL | 10 μg/mL | 20 μg/mL |
| sodium chloride | 8.0 mg/mL | 8.0 mg/mL | 8.0 mg/mL | 8.0 mg/mL | 8.0 mg/mL |
| citric acid |  |  |  |  | 3.706 mg/mL |
| sodium dihydrogen phosphate | 0.425 mg/mL | 0.425 mg/mL | 0.425 mg/mL | 0.425 mg/mL |  |
| disodium hydrogen phosphate | 2.50 mg/mL | 2.50 mg/mL | 2.50 mg/mL | 2.50 mg/mL | 590 mg/mL |

|  | Preparation Example 6 | Preparation Example 7 | Preparation Example 8 | Preparation Example 9 | Preparation Example 10 |
|---|---|---|---|---|---|
| polyvinyl alcohol | 10.0 mg/mL |  |  |  |  |
| Carbomer 940 |  | 8.0 mg/mL | 6.0 mg/mL | 6.0 mg/mL | 5.0 mg/mL |
| triethanolamine |  | 6.0 mg/mL | 5.0 mg/mL | 5.0 mg/mL | 5.0 mg/mL |
| rh-bFGF | 5000 IU/mL | 4500 IU/mL | 4200 IU/mL | 4500 IU/mL | 4200 IU/mL |
| glycerol |  | 25.0 mg/mL | 25.0 mg/mL | 25.0 mg/mL | 25.0 mg/mL |
| human serum albumin | 0.25 mg/mL | 0.30 mg/mL | 0.30 mg/mL | 0.30 mg/mL | 0.20 mg/mL |
| heparin sodium | 25 μg/mL | 70 μg/mL | 70 μg/mL | 70 μg/mL | 50 μg/mL |
| sodium chloride | 8.0 mg/mL |  |  |  |  |
| citric acid | 3.706 mg/mL |  |  |  |  |
| sodium dihydrogen phosphate |  |  |  |  |  |
| disodium hydrogen phosphate | 590 mg/mL |  |  |  |  |

Preparation Example 1

(1) 1.0 g of polyvinyl alcohol was dispersed and dissolved in an appropriate amount of water for injection, autoclaved, cooled to room temperature, and ready for use;

(2) 500000 IU of recombinant human-basic fibroblast growth factor, 25 mg of human serum albumin, 2.5 mg of heparin sodium, 800 mg of sodium chloride, 42.5 mg of sodium dihydrogen phosphate, and 250 mg of disodium hydrogen phosphate were dissolved in an appropriate amount of water for injection, and sterile filtered through a 0.22 μm filter membrane;

(4) The sterile solution was filled by using a three-in-one filling machine of blowing, filling and sealing, and the filling amount was 0.4 mL, and thus the finished product was obtained.

Preparation Example 3

(1) 1.0 g of polyvinyl alcohol was dispersed and dissolved in an appropriate amount of water for injection, autoclaved, cooled to room temperature, and ready for use;

(2) 420000 IU of recombinant human-basic fibroblast growth factor, 20 mg of human serum albumin, 2.0 mg of heparin sodium, 800 mg of sodium chloride, 42.5 mg of sodium dihydrogen phosphate, and 250 mg of disodium hydrogen phosphate were dissolved in an appropriate amount of water for injection, and sterile filtered through a 0.22 μm filter membrane;

(3) The solutions obtained in the step (1) and in the step (2) were uniformly mixed under a sterile condition, made up to 100 mL with sterile water for injection, and thus obtained;

(4) The sterile solution was filled by using a three-in-one filling machine of blowing, filling and sealing, and the filling amount was 0.4 mL, and thus the finished product was obtained.

Preparation Example 4

(1) 1.5 g of polyvinyl alcohol was dispersed and dissolved in an appropriate amount of water for injection, autoclaved, cooled to room temperature, and ready for use;

(2) 420000 IU of recombinant human-basic fibroblast growth factor, 10 mg of human serum albumin, 1.0 mg of heparin sodium, 800 mg of sodium chloride, 42.5 mg of sodium dihydrogen phosphate, and 250 mg of disodium hydrogen phosphate were dissolved in an appropriate amount of water for injection, and sterile filtered through a 0.22 μm filter membrane;

(3) The solutions obtained in the step (1) and in the step (2) were uniformly mixed under a sterile condition, made up to 100 mL with sterile water for injection, and thus obtained;

(4) The sterile solution was filled by using a three-in-one filling machine of blowing, filling and sealing, and the filling amount was 0.4 mL, and thus the finished product was obtained.

Preparation Example 5

(1) 1.0 g of polyvinyl alcohol was dispersed and dissolved in an appropriate amount of water for injection, autoclaved, cooled to room temperature, and ready for use;

(2) 420000 IU of recombinant human-basic fibroblast growth factor, 20 mg of human serum albumin, 2.0 mg of heparin sodium, 800 mg of sodium chloride, 370.6 mg of citric acid, and 5.9 g of disodium hydrogen phosphate were dissolved in an appropriate amount of water for injection, and sterile filtered through a 0.22 μm filter membrane;

(3) The solutions obtained in the step (1) and in the step (2) were uniformly mixed under a sterile condition, made up to 100 mL with sterile water for injection, and thus obtained;

(4) The sterile solution was filled by using a three-in-one filling machine of blowing, filling and sealing, and the filling amount was 0.4 mL, and thus the finished product was obtained.

Preparation Example 6

(1) 1.0 g of polyvinyl alcohol was dispersed and dissolved in an appropriate amount of water for injection, autoclaved, cooled to room temperature, and ready for use;

(2) 500000 IU of recombinant human-basic fibroblast growth factor, 25 mg of human serum albumin, 2.5 mg of heparin sodium, 800 mg of sodium chloride, 370.6 mg of citric acid, and 5.9 g of disodium hydrogen phosphate were dissolved in an appropriate amount of water for injection, and sterile filtered through a 0.22 μm filter membrane;

(3) The solutions obtained in the step (1) and in the step (2) were uniformly mixed under a sterile condition, made up to 100 mL with sterile water for injection, and thus obtained;

(4) The sterile solution was filled by using a three-in-one filling machine of blowing, filling and sealing, and the filling amount was 0.4 mL, and thus the finished product was obtained.

Preparation Example 7

(1) 0.80 g of Carbomer 940 was weighted and dispersed in an appropriate amount of room temperature water for injection, stirred for 60-120 min, swelled overnight, and ready for use;

(2) 0.60 g of triethanolamine was added to the Carbomer 940 dispersion, stirred into a transparent uniform gel base, and then subjected to moist heat sterilization (121° C., 30 min), cooled to room temperature after sterilization was completed, and ready for use;

(3) 2.50 g of glycerol, 30.0 mg of human serum albumin, 7.0 mg of heparin sodium, and 450000 IU of recombinant human-basic fibroblast growth factor were added into an appropriate amount of room temperature water for injection, stirred uniformly, and then passed through a 0.22 μm filter membrane under a sterile condition, mixed with the gel base in the step (2), and then quantified and stirred uniformly;

(4) The sterile gel was filled by using a three-in-one filling machine of blowing, filling and sealing, and the filling amount was 0.4 g, and thus the finished product was obtained.

Preparation Example 8

(1) 0.60 g of Carbomer 940 was weighted and dispersed in an appropriate amount of room temperature water for injection, stirred for 60-120 min, swelled overnight, and ready for use;

(2) 0.50 g of triethanolamine was added to the Carbomer 940 dispersion, stirred into a transparent uniform gel base, and then subjected to moist heat sterilization (121° C., 30 min), cooled to room temperature after sterilization was completed, and ready for use;

(3) 2.50 g of glycerol, 30.0 mg of human serum albumin, 7.0 mg of heparin sodium, and 420000 IU of recombinant human-basic fibroblast growth factor were added into an appropriate amount of room temperature water for injection, stirred uniformly, and then passed through a 0.22 μm filter membrane under a sterile condition, mixed with the gel base in the step (2), and then quantified and stirred uniformly;

(4) The sterile gel was filled by using a three-in-one filling machine of blowing, filling and sealing, and the filling amount was 0.4 g, and thus the finished product was obtained.

Preparation Example 9

(1) 0.60 g of Carbomer 974 was weighted and dispersed in an appropriate amount of room temperature water for injection, stirred for 60-120 min, swelled overnight, and ready for use;

(2) 0.50 g of triethanolamine was added to the Carbomer 974 dispersion, stirred into a transparent uniform gel base, and then subjected to moist heat sterilization (121° C., 30 min), cooled to room temperature after sterilization was completed, and ready for use;

(3) 2.50 g of glycerol, 30.0 mg of human serum albumin, 7.0 mg of heparin sodium, and 450000 IU of recombinant human-basic fibroblast growth factor were added into an appropriate amount of room temperature water for injection, stirred uniformly, and then passed through a 0.22 μm filter membrane under a sterile condition, mixed with the gel base in the step (2), and then quantified and stirred uniformly;

(4) The sterile gel was filled by using a three-in-one filling machine of blowing, filling and sealing, and the filling amount was 0.4 g, and thus the finished product was obtained.

Preparation Example 10

(1) 0.50 g of Carbomer 974 was weighted and dispersed in an appropriate amount of room temperature water for injection, stirred for 60-120 min, swelled overnight, and ready for use;

(2) 0.50 g of triethanolamine was added to the Carbomer 974 dispersion, stirred into a transparent uniform gel base, and then subjected to moist heat sterilization (121° C., 30 min), cooled to room temperature after sterilization was completed, and ready for use;

(3) 2.50 g of glycerol, 20.0 mg of human serum albumin, 5.0 mg of heparin sodium, and 420000 IU of recombinant human-basic fibroblast growth factor were added into an appropriate amount of room temperature water for injection, stirred uniformly, and then passed through a 0.22 μm filter membrane under a sterile condition, mixed with the gel base in the step (2), and then quantified and stirred uniformly;

(4) The sterile gel was filled by using a three-in-one filling machine of blowing, filling and sealing, and the filling amount was 0.4 g, and thus the finished product was obtained.

Example 4. Stability Study

1) Study of the Effect of Amino Acids on the Stability of the Rh-bFGF Stock Solution The rh-bFGF stock solution itself is unstable in nature, and tends to polymerize and thus precipitate at room temperature. Therefore, different stabilizers were selected and used, and primarily screened for the stability of the stock solution. 5% and 2% mannitol, 5% and 2% glycine, and 2% dextran were selected and used, and allowed to stand at 25° C. environment for 17 days. Protein concentrations were measured on days 0, 7, and 17, respectively, and the results are shown in Table 3.

TABLE 3

Rate of change in protein concentration of the rh-bFGF stock solution in the screening test of stabilizers

| Sample | Day 0 | Day 7 | Day 17 |
|---|---|---|---|
| No stabilizer | 100.00% | 29.96% | 13.63% |
| 5% mannitol | 100.00% | 49.80% | 17.31% |
| 2% mannitol | 100.00% | 53.29% | 15.66% |
| 5% glycine | 100.00% | 95.67% | 86.26% |
| 2% glycine | 100.00% | 94.74% | 82.73% |
| 2% dextran | 100.00% | 51.65% | 16.20% |

The results showed that 5% glycine was effective in preventing protein from precipitation. There remained 86.26% protein after being placed under the thermal destructive condition for 17 days. After 17 days, the effect of glycine was significantly better than that of mannitol and dextran, while only 13.6% of the protein was left with no stabilizer added.

Figure 7:
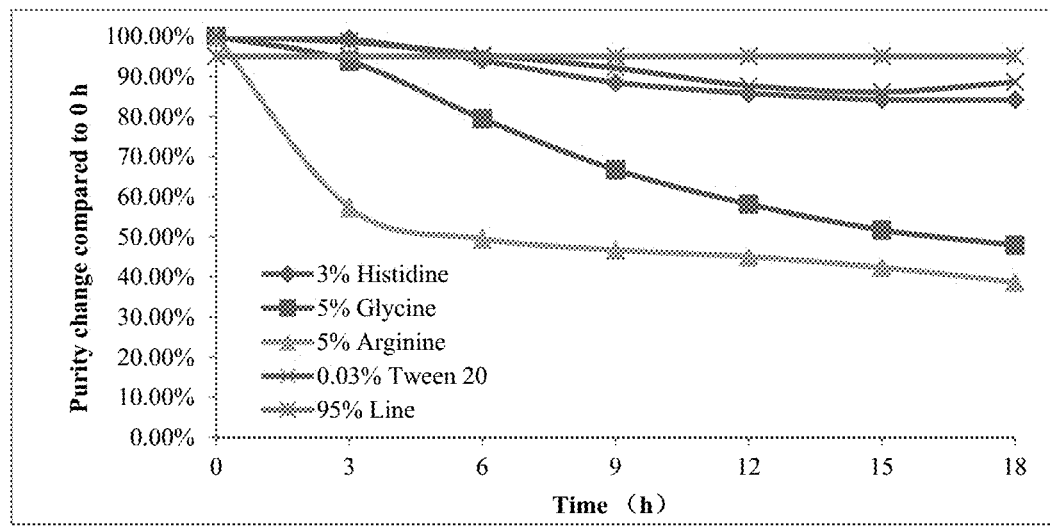
FIG. 7 shows the effect of different amino acids, including histidine, glycine and arginine, and Tween on the purity change of rh-bFGF under the hot stress condition, wherein 95% LINE refers to the quality standard for the purity of the rh-bFGF stock solution; and a purity of less than 95% for the stock solution means that the purity is unqualified.

2) Study of the Effect of Histidine on the Stability of the Rh-bFGF Stock Solution Different amino acids (glycine, histidine, arginine) and Tween 20 were selected and used, and further screened for the stability of the stock solution, and allowed to stand at 25° C. environment for 18 h. The results are shown in FIG. 7.

The results showed that 3% histidine and 0.03% Tween 20 were more effective than 5% glycine with respect to the stability of the rh-bFGF stock solution. The purity of the protein could still be maintained above 85% after being placed under the thermal destructive condition for 18 h. Histidine and Tween 20 were superior to glycine in protecting rh-bFGF.

3) Study of the Effect of HSA on the Stability of Rh-bFGF Stock Solution

Figure 8:
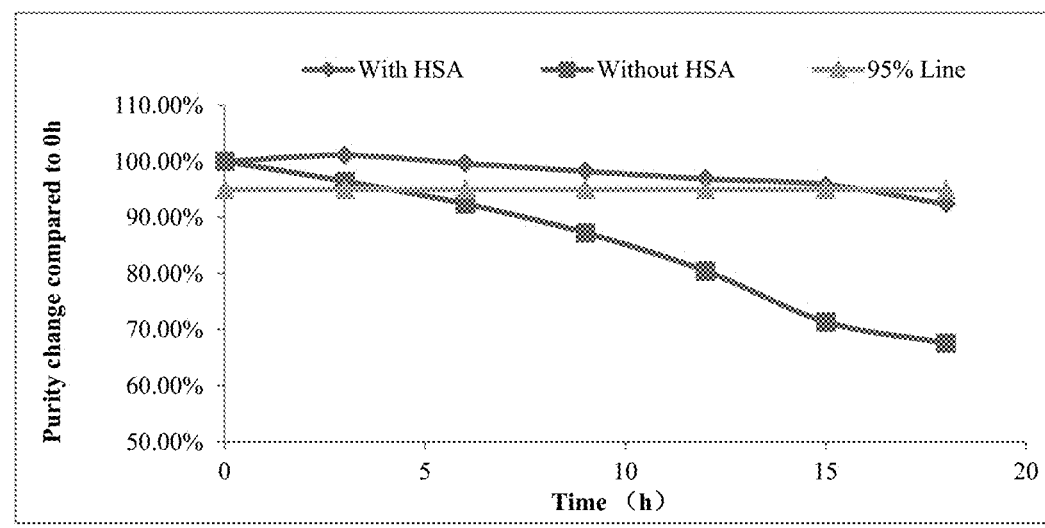
FIG. 8 shows the effect of HSA on the purity change of rh-bFGF under the hot stress condition.

Since HSA would interfere with the determination of protein content, the stock solutions with or without HSA were placed at 25° C. environment for 18 h, and change in the purity of the protein after being subjected to heat-damage was detected by high-resolution chromatography. The results are shown in FIG. 8.

The results showed that HSA could significantly improve the stability of rh-bFGF. With a change rate of 95% purity as an indicator, samples containing no HSA can only be maintained for 4 h under the stress condition, and can be extended to 15 hours after addition of HSA. It has been shown that HSA is an excellent protein protectant for bFGF.

Example 5. Study on the Efficacy in an Animal Dry Eye Model

In this study, New Zealand rabbit dry eye model was selected and used, the clinical indicators (tear secretion, and tear film break-up time) of the model were observed, and the clinical treatment effect of the medicament for dry eye was evaluated. New Zealand rabbits were divided into negative control group (Negative control, untreated), model control group (Model, treated with alkali burn but no any eye drops were added), treatment group with sodium hyaluronate eye drop (HA group), and the Group D (4.0 μg/mL), E (8.0 μg/mL), F (16.0 μg/mL), and G (32.0 μg/mL) which were divided according to the concentration of the rh-bFGF eye drops of Preparation Example 3 as used. The negative control group had 72 rabbits/group, and the remaining groups had 8 rabbits/group. The dosage was 300 μl/eye/day.

(1) Method for Measuring the Amount of Tear Secretion (Both Eyes) (the Wet Length of Phenol Red Cotton Thread):

The secretion of tears from New Zealand rabbits was measured using the Schirmer I test. That is, the phenol red cotton thread was clamped with ophthalmic forceps, and placed in the outer canthus of the New Zealand rabbit. After 60 s, the phenol red cotton thread was taken out and measured for the wet length. The phenol red cotton thread turned red after being wet, and the eye wetness was determined according to the wet length. The experimental results are shown in FIG. 9.

Figure 9:
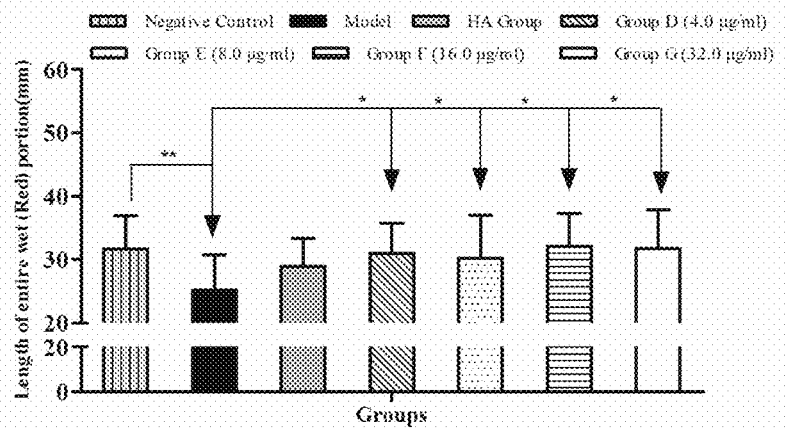
FIG. 9 shows the effect of different concentrations of the rh-bFGF eye drop on tear secretion in a dry eye model of alkali burned New Zealand rabbits. The symbol "*" or "**" indicates a significant difference ($p<0.05$ or $p<0.01$).

As shown in FIG. 9, the wet lengths of the phenol red cotton thread in the model control group all were significantly decreased as compared with those in the negative control eyes. On day 10 of administration, the wet lengths of the phenol red cotton thread in the rh-bFGF eye drops D, E, F, and G groups all were significantly longer with statistically significant differences, as compared with the model control group.

(2) Method for Measuring Tear Film Break-Up Time (Both Eyes):

2 μl of 0.5% sodium fluorescein solution was instilled into the lower eyelid conjunctival sac of New Zealand rabbit eyes using an adjustable pipette. After several times of manual blinking with constant force, the rabbit eyes were opened with a constant force and the cornea was observed with a slit lamp microscope and cobalt blue light. When a black area appears in the corneal green film, the tear film is indicated to be broken. Three measurements were taken continuously and the average value was taken. Less than 10 seconds of the tear film break-up time indicates that the tear film is unstable, which is a prominent marker of KCS caused by the lack of mucin in tears, suggesting that the goblet cells of the conjunctiva are seriously damaged or lost, and it is easy to cause dry eye. The experimental results are shown in FIG. 10.

Figure 10:
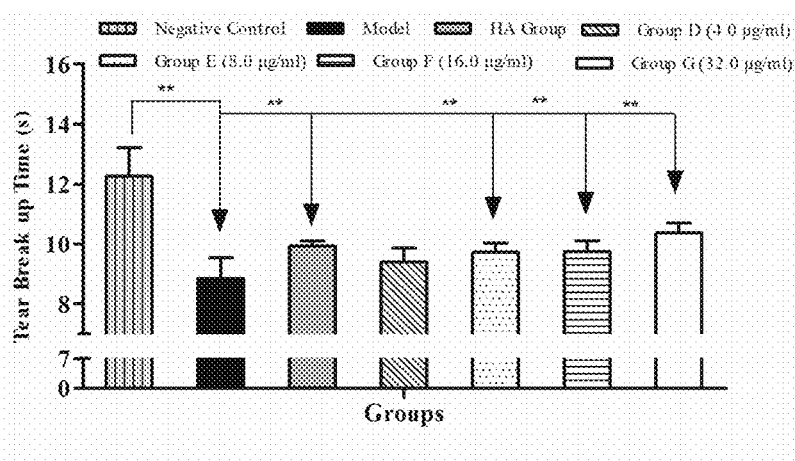
FIG. 10 shows the effect of different concentrations of the rh-bFGF eye drop on the break-up time of the tear film in a dry eye model of alkali burned New Zealand rabbits. The symbol "*" or "**" indicates a significant difference ($p<0.05$ or $p<0.01$).

As shown in FIG. 10, the tear film break-up times of the model control group all were significantly shorter than those of the negative control eyes on day 10 of administration, as compared to the negative control eyes. On day 10 of administration, the tear film break-up time of the rh-bFGF eye drops D, E, F, and G groups all were significantly prolonged with statistically significant differences, as compared with the model control group.

In summary, the results of the phenol red cotton thread test of the tear secretion showed that the eye drops of the present invention could improve the tear secretion amount of the model animals (see FIG. 9); the tear film break-up time test showed that there was a significant improvement in the tear film break-up time in the dry eye model (see FIG. 10). With an increase in dosage, rh-bFGF eye drops had a significant improvement on the dry eye model of alkal burned New Zealand rabbits.

Various modifications, substitutions, changes and equivalents will occur to those skilled in the art, although some features of the present invention has been set forth and illustrated herein. Therefore, it is to be understood that the appended claims are intended to cover all such modifications and changes that fall into the true spirit and scope of the present invention.

The invention claimed is:

1. A method of producing a soluble recombinant human-basic fibroblast growth factor (rh-bFGF), the method comprising:
   culturing a host cell comprising a mutated nucleic acid molecule encoding the rh-bFGF;
   expressing the rh-bFGF in the host cell under a condition suitable for expression of the rh-bFGF; and
   recovering the rh-bFGF by purification, wherein said mutated nucleic acid molecule comprises a sequence selected from the group consisting of SEQ ID NO: 1, SEQ ID NO: 2, or SEQ ID NO: 3.

2. The method of claim 1, wherein the sequence of the mutated nucleic acid molecule is SEQ ID NO: 1.

3. The method of claim 1, wherein the host cell is *Escherichia coli*.

4. A mutated nucleic acid molecule encoding a recombinant human-basic fibroblast growth factor, which comprises a sequence selected from the group consisting of SEQ ID NO: 1, SEQ ID NO: 2, or SEQ ID NO: 3.

5. The mutated nucleic acid molecule of claim 4 which has the sequence of SEQ ID NO: 1.

6. A vector comprising the mutated nucleic acid molecule of claim 4 or 5.

7. The vector of claim 6 wherein said vector is pET-30a (+).

* * * * *

SEQUENCE LISTING

<160> NUMBER OF SEQ ID NOS: 6

<210> SEQ ID NO 1
<211> LENGTH: 468
<212> TYPE: DNA
<213> ORGANISM: Artificial Sequence
<220> FEATURE:
<223> OTHER INFORMATION: Synthetic

<400> SEQUENCE: 1

```
atggctgctg gttcgattac gacgctgccg gctctgccgg aagatggtgg ttcaggtgca      60
tttccgccgg gtcactttaa ggatccgaaa cgtctgtatt gcaagaacgg cggcttttc      120 ctgcgcattc atccggatgg ccgtgtcgac ggtgtgcgcg aaaaaagcga tccgcacatt      180
aagctgcagc tgcaagcaga agaacgtggc gtggttagca tcaaaggtgt ttgtgcgaac      240
cgttacctgg ccatgaaaga agatggccgc ctgctggcta gtaagtgcgt caccgacgaa      300 tgcttttct ttgaacgtct ggaatccaac aattataata cctaccgtag ccgcaaatat      360
acgtcttggt atgtggccct gaaacgcacg ggccagtata agctgggttc caaaacgggt      420
ccgggtcaaa aagccattct gttcctgccg atgtccgcaa aatcataa      468
```

<210> SEQ ID NO 2
<211> LENGTH: 468
<212> TYPE: DNA
<213> ORGANISM: Artificial Sequence
<220> FEATURE:
<223> OTHER INFORMATION: Synthetic

<400> SEQUENCE: 2

```
atggctgctg gttctatcac cacctgccg gctctgccgg aagacggtgg ttctggtgct      60
ttcccgccgg gtcacttcaa agacccgaaa cgtctgtact gcaaaaacgg tggtttcttc      120
ctgcgtatcc acccggacgg tcgtgttgac ggtgttcgtg aaaaatctga cccgcacatc      180
aaactgcagc tgcaggctga agaacgtggt gttgtttcta tcaaaggtgt ttgcgctaac      240
cgttacctgg ctatgaaaga agacggtcgt ctgctggctt ctaaatgcgt taccgacgaa      300
tgcttcttct tcgaacgtct ggaatctaac aactacaaca cctaccgttc tcgtaaatac      360
acctcttggt acgttgctct gaaacgtacc ggtcagtaca aactgggttc taaaaccggt      420
```

```
ccgggtcaga aagctatcct gttcctgccg atgtctgcta aatcttaa       468
```

<210> SEQ ID NO 3
<211> LENGTH: 468
<212> TYPE: DNA
<213> ORGANISM: Artificial Sequence
<220> FEATURE:
<223> OTHER INFORMATION: Synthetic

<400> SEQUENCE: 3

```
atggcagccg gtagcatcac caccctgccg gccctgccgg aggatggcgg cagcggcgcc    60
ttcccgccgg ccacttcaa  ggaccccgaag cgtctgtact gcaaaaacgg tggcttcttc   120
ctgcgcatcc accggacgg  ccgtgttgac ggtgtccgtg agaagagcga ccctcacatc   180
aagctgcaac tgcaagcaga gagcgtggt  gttgtgtcta tcaaaggtgt gtgtgctaac   240
cgttacctgg ctatgaagga gatggtcgt  ctgctggctt ctaaatgtgt taccgatgag   300
tgtttcttttt tgaacgtct  ggaatctaac aactacaaca cttaccgttc tcgtaaatac   360
acctcttggt atgtggcact gaaacgtact ggtcagtata aactgggttc caaaaccggt   420
cctggtcaga aagctatcct gtttctgcca atgtctgcta agagctaa              468
```

<210> SEQ ID NO 4
<211> LENGTH: 468
<212> TYPE: DNA
<213> ORGANISM: Homo Sapien

<400> SEQUENCE: 4

```
atggcagccg ggagcatcac cacgctgccc gccttgcccg aggatggcgg cagcggcgcc    60
ttcccgcccg ccacttcaa  ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga gagagagga  gttgtgtcta tcaaaggagt gtgtgctaac   240
cgttacctgg ctatgaagga gatggaaga  ttactggctt ctaaatgtgt tacgatgag    300
tgtttcttttt tgaacgatt  ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga              468
```

<210> SEQ ID NO 5
<211> LENGTH: 155
<212> TYPE: PRT
<213> ORGANISM: Homo Sapien

<400> SEQUENCE: 5

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
```

```
                    100                 105                 110
Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 6
<211> LENGTH: 155
<212> TYPE: PRT
<213> ORGANISM: Artificial Sequence
<220> FEATURE:
<223> OTHER INFORMATION: Synthetic

<400> SEQUENCE: 6

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155
```